(12) United States Patent
Lu et al.

(10) Patent No.: US 10,617,768 B2
(45) Date of Patent: Apr. 14, 2020

(54) ENGINEERED EXOSOMES FOR THE DELIVERY OF BIOACTIVE CARGO USING TRANSMEMBRANE TETRASPANINS

(71) Applicant: Santa Clara University, Santa Clara, CA (US)

(72) Inventors: Biao Lu, San Francisco, CA (US); Conary Meyer, Santa Clara, CA (US); Joseph Losacco, Lake Forest, IL (US); Zachary Stickney, Mercer Island, WA (US)

(73) Assignee: Santa Clara University, Santa Clara, CA (US)

( * ) Notice: Subject to any disclaimer, the term of this patent is extended or adjusted under 35 U.S.C. 154(b) by 78 days.

(21) Appl. No.: 15/648,215

(22) Filed: Jul. 12, 2017

(65) Prior Publication Data

US 2018/0015182 A1 Jan. 18, 2018

Related U.S. Application Data

(60) Provisional application No. 62/361,295, filed on Jul. 12, 2016.

(51) Int. Cl.
| | |
|---|---|
| *A61K 47/69* | (2017.01) |
| *A61K 38/02* | (2006.01) |
| *A61K 38/43* | (2006.01) |
| *A61K 39/12* | (2006.01) |
| *A61K 39/00* | (2006.01) |
| *A61K 47/65* | (2017.01) |
| *A61K 47/62* | (2017.01) |
| *C07K 14/705* | (2006.01) |

(52) U.S. Cl.
CPC .......... *A61K 47/6901* (2017.08); *A61K 38/02* (2013.01); *A61K 38/43* (2013.01); *A61K 39/0011* (2013.01); *A61K 39/12* (2013.01); *A61K 47/62* (2017.08); *A61K 47/65* (2017.08); *A61K 2039/6006* (2013.01); *A61K 2039/627* (2013.01); *A61K 2039/64* (2013.01); *C07K 14/70503* (2013.01); *C07K 14/70596* (2013.01); *C07K 2317/622* (2013.01); *C07K 2319/03* (2013.01); *C07K 2319/21* (2013.01); *C07K 2319/32* (2013.01); *C07K 2319/60* (2013.01); *C07K 2319/85* (2013.01)

(58) Field of Classification Search
None
See application file for complete search history.

(56) References Cited

U.S. PATENT DOCUMENTS 8,697,439 B2    4/2014    Mangeot

FOREIGN PATENT DOCUMENTS

WO    WO2017054086    4/2017

OTHER PUBLICATIONS

Mangeot et al. 2011. Protein Transfer Into Human Cells by VSV-G-induced Nanovesicles. www.moleculartherapy.org vol. 19 No. 9, 1656-1666 Sep. 2011.

*Primary Examiner* — Suzanne M Noakes
(74) *Attorney, Agent, or Firm* — Lumen Patent Firm

(57) ABSTRACT

Engineered exosomes for the delivery of bioactive cargo are provided. The exosomes incorporate a tetraspanin transmembrane anchoring scaffold onto the membrane of the exosome. The tetraspanin transmembrane anchoring scaffold has a C-terminal attachment site in the inner-vesicle space of the exosome, a N-terminal attachment site in the inner-vesicle space or the outer-vesicle space, and/or a loop attachment site in the outer-vesicle space. Peptides can be attached to the different attachments sites in any form or combination. Tetrapanins naturally anchor on the exosome membrane, are biocompatible, and allow for robust loading and delivery of bioactive cargos in mammalian system.

6 Claims, 7 Drawing Sheets
Specification includes a Sequence Listing.

FIG. 2A
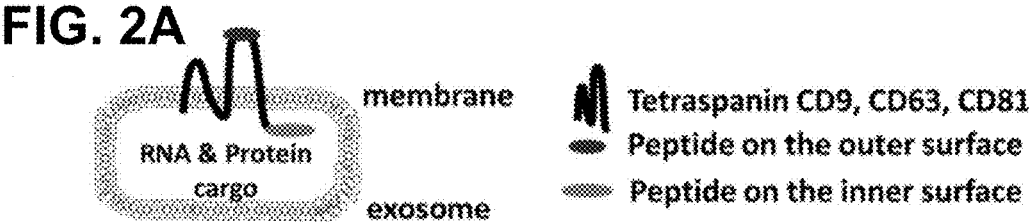
FIG. 2B
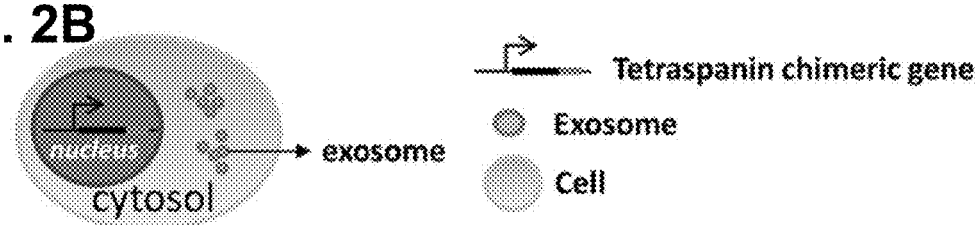
FIG. 2C
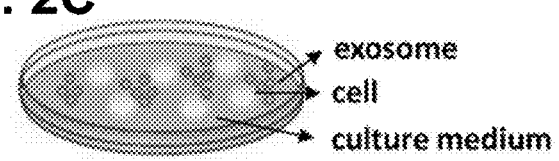
FIG. 2D
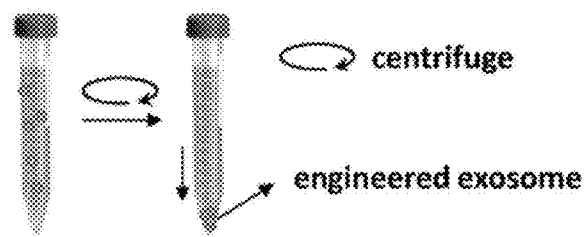
FIG. 2E
Nano-particle analysis
FIG. 2F
Potential applications
- Exosome track and image
- Targeted drug delivery
- Therapeutics
- Protein-protein interaction
- Vaccine

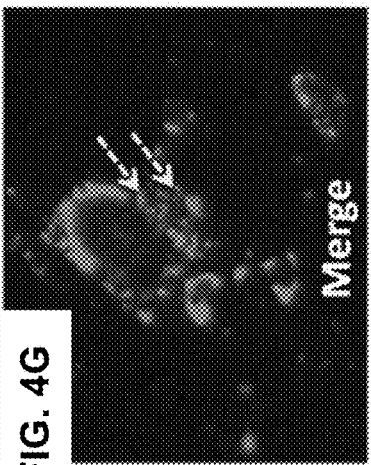
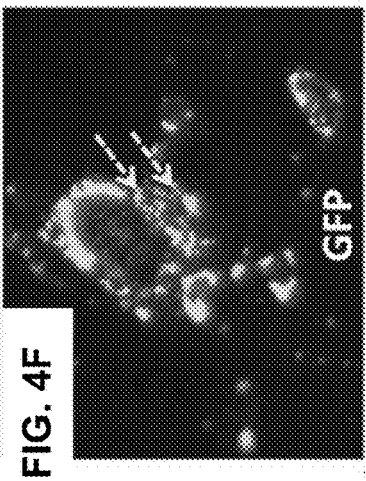
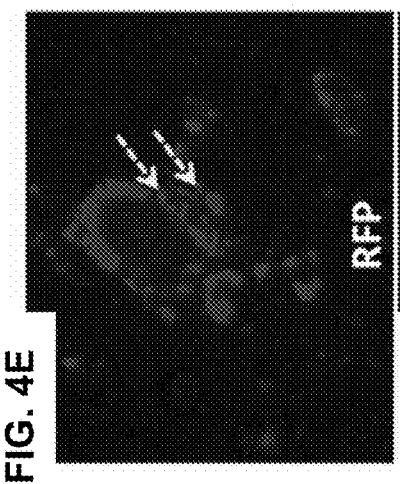
FIG. 4E
FIG. 4F
FIG. 4G
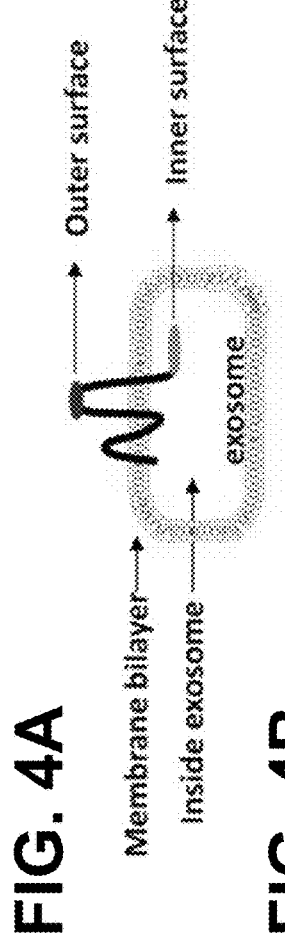
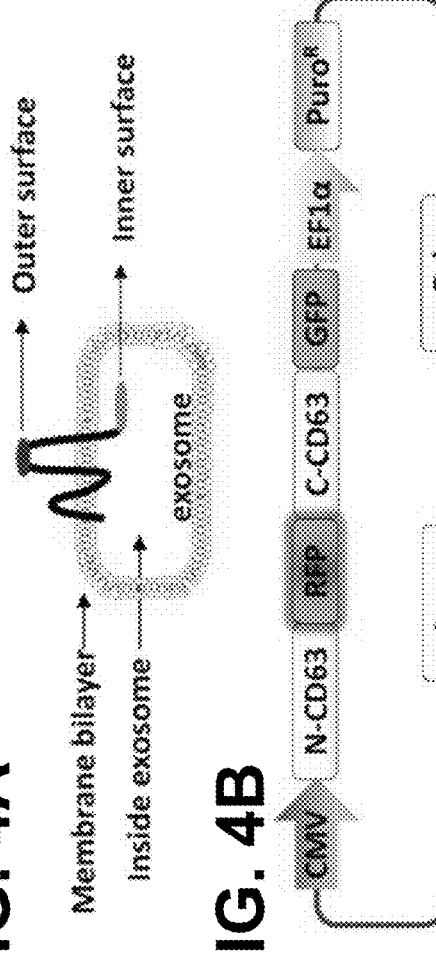
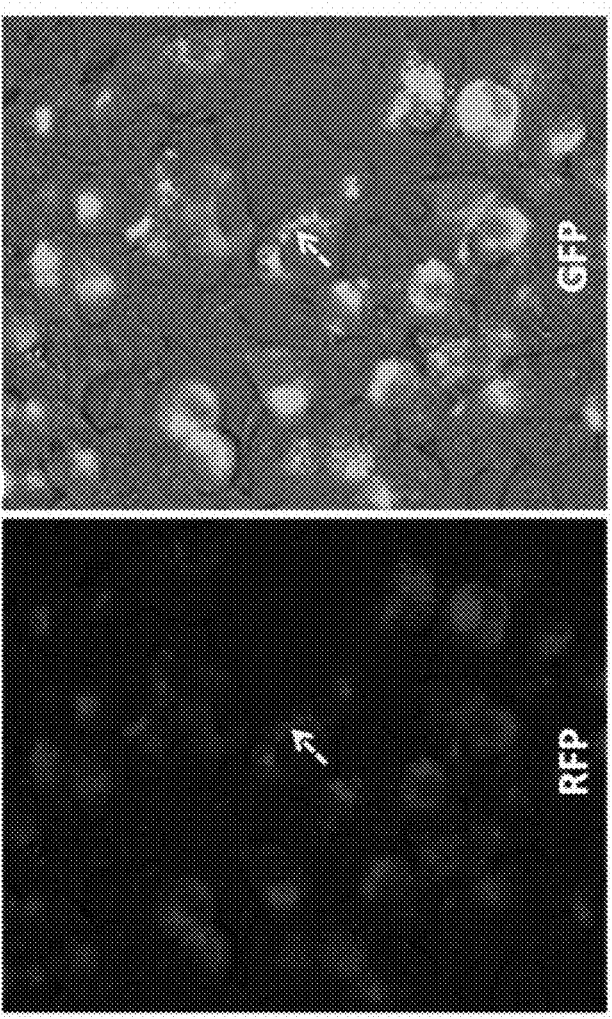
FIG. 4A
FIG. 4B
FIG. 4C
FIG. 4D

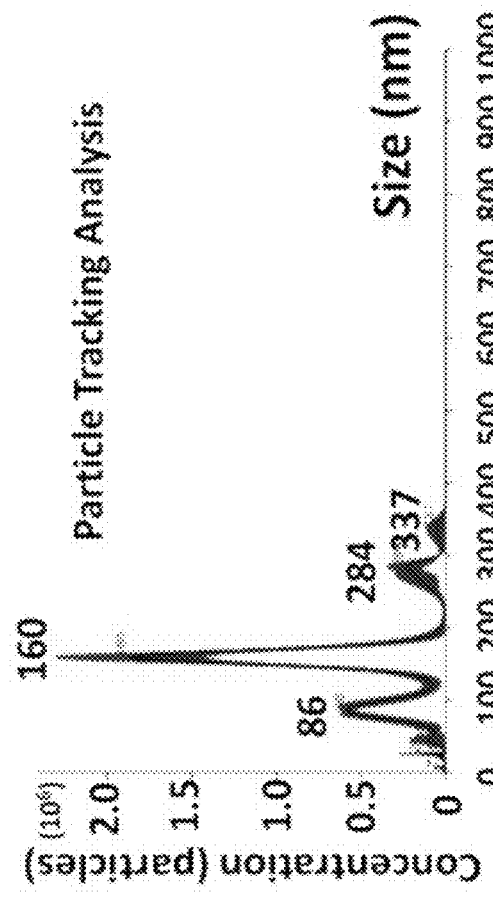
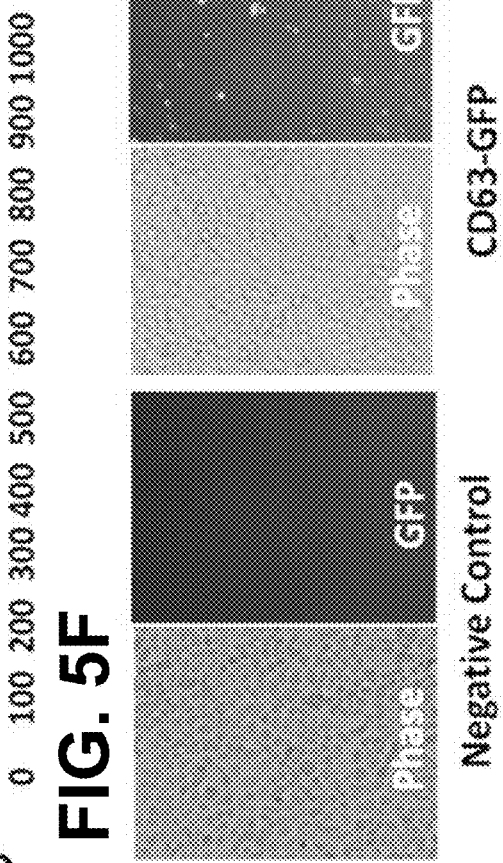
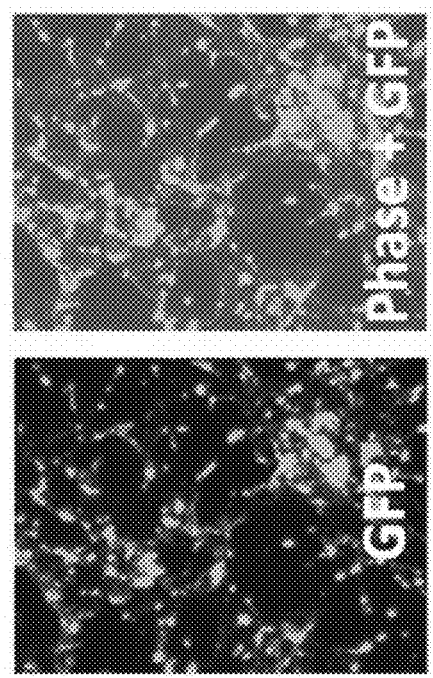
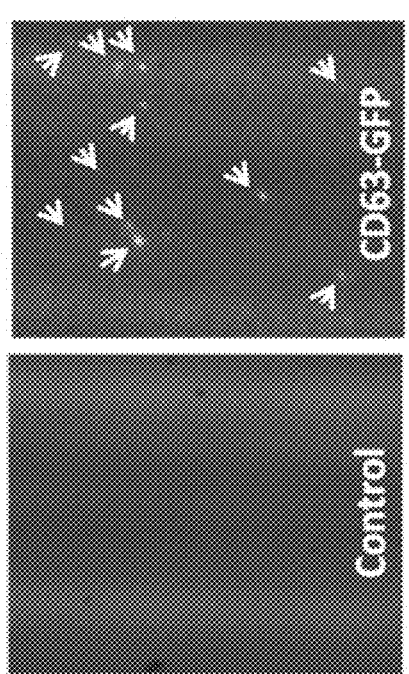
FIG. 5A  FIG. 5B  FIG. 5C  FIG. 5D  FIG. 5E  FIG. 5F

ENGINEERED EXOSOMES FOR THE DELIVERY OF BIOACTIVE CARGO USING TRANSMEMBRANE TETRASPANINS

CROSS-REFERENCE TO RELATED APPLICATIONS

This application claims priority from U.S. Provisional Patent Application 62/361,295 filed Jul. 12, 2016, which is incorporated herein by reference.

SEQUENCE LISTING

This application includes a sequence listing submitted in written form and in computer readable form.

FIELD OF THE INVENTION

This invention relates to delivery of bioactive cargo using engineered exosomes.

BACKGROUND OF THE INVENTION

Protein therapeutics is one of the fastest growing classes of biologics in medicine, and has achieved widespread success in combating various difficult-to-treat human disorders including cancer, cardiovascular and autoimmune disease.

The efficacy and specificity of protein therapeutics largely depend on an efficient and robust method for targeted protein delivery. Although proven to be effective for extracellular targets, current methods of protein delivery (such as artificial liposome or synthesized polymers) have limitations for intracellular processes, mainly owing to their inability to enter mammalian cells. Therefore, efficient technology of intracellular delivery is essential to fully realize the potential of protein therapeutics. The present invention advances the art by providing engineered exosomes for the delivery of bioactive cargo using transmembrane tetraspanins.

SUMMARY OF THE INVENTION

Successfully displaying a candidate protein onto the surface of exosomes requires a sound strategy and the ability to overcome a number of technical hurdles. The first key step was to identify a native surface protein to serve as anchoring scaffold. We utilized tetraspanins CD9, CD63, and CD81, as they are the surface markers of all exosomes. Second, we focused on the multi-trans-membrane configuration of CD63 and successfully identified two candidate sites for displaying the fusion proteins on both inner and outer surfaces of the exosome. Third, we validated our system by demonstrating the correct intracellular partitioning of engineered protein into the proper endosomal compartments and eventually secreted exosomes into the culture medium. Lastly, by establishing the stably engineered HEK293 cells, we demonstrated the ability of this robust system to continuously produce, secret and uptake displayed exosomes with minimal effects on normal cell biology.

The ability to specifically engineer nano-vesicle exosomes has far-reaching implications in basic and applied biomedical fields. As demonstrated in this invention, exosome surface displaying of fluorescent reporters provides an effective way for investigating biogenesis, secretion and up-take of exosomes. It is conceivable that by presenting a molecule such as single chain variable fragment (ScFv) of antibody on the outer surface of exosomes, a targeted delivery system may be engineered. Similarly, by tagging a therapeutic protein on the inner surface of exosomes, one may devise new exosome-based therapeutics with the use of the exosome surface display system of this invention.

Accordingly, this invention teaches tetraspanin as a delivery mechanism for bioactive cargo. Bioactive cargo that could be attached to tetraspanin is a 6×His tag for exosome purification, an imaging protein (e.g. GFP or RFP or luciferase), a viral antigen epitope, a cancer antigen epitope, a protein drug (e.g. decoy receptors, single chain antibody, suicide genes), a suicide gene, or a therapeutic protein for replacement therapy.

Generally speaking the invention pertains to embodiments of an engineered exosome for the delivery of bioactive cargo/protein. The proteins could be attached to one, two or three different attachments sites. The invention includes embodiments of an engineered exosome for the delivery of bioactive cargo with different combinations of the described cargo or attachment sites. In these embodiments, an exosome defining an inner-vesicle space and an outer-vesicle space. The exosome incorporates a tetraspanin transmembrane anchoring scaffold onto the membrane of the exosome.

List of Definitions

Bioactive cargo=macromolecules namely proteins, nucleic acids, and lipids
RFP=red fluorescent protein
GFP=creen fluorescent protein
CMV=constitutive cytomegalovirus promoter
MVB=multi-vesicular body
Amp=Ampicillin resistant gene
Ori=origin of replication
Puro=puromycin resistant gene
EF1α=elongation factor 1 alpha promoter
CD63 (wild-type)=the wild-type tetraspanin protein CD63
CD63 (full length)=the wild-type and untruncated CD63
CD63 (truncated length)=the shortened CD63
CD9=tetraspanin protein CD9
CD81=tetraspanin protein CD81

BRIEF DESCRIPTION OF THE DRAWINGS

In FIG. 1A, the biogenesis of exosome starts at inward budding of late endosome membrane and finishes when the MVB fuses with the plasma membrane and releases the exosomes into the extracellular space. In FIG. 1B, exosomes are nano-vesicles that are enriched with certain proteins and nucleic acids.

FIGS. 2A-F show according to an exemplary embodiment of the invention system design of surface engineering of exosome. (FIG. 2A) Schematic of Surface engineering of exosome via tetraspanin proteins. CD63 is a "M" shape transmembrane protein with two termini and small middle loop on inner surface while two other loops exist on the outer surface of the exosome. Peptides can be fused with CD63 either at the second loop (outer surface display; 'red' oval) or the C-terminus (inner surface display; 'green' oval). (FIG. 2B) Delivery of CD63 fusion genes into living cells will partition the displayed fluorescent marker ('green') on the surface of exosome via CD63 anchoring. (FIGS. 2C-D) Engineered exosomes are released into the culture medium that can be recovered with polymer-based precipitation solution and centrifugation. (FIG. 2E) Enriched exosomes can be used for analysis or characterization. (FIG. 2F) A list of potential applications. For interpretation of the references to color in this figure legend, the reader is referred to our paper: Stickney et al. (2016) Development of exosome surface display technology in living human cells, Biochemical and Biophysical Research Communications 472: 53-59.

(FIG. 3A) Mammalian expression vector and the configuration of CD63-GFP. Promoter sequences derived from cytomegalovirus (CMV) or elongation factor 1 alpha (EF1a) are used to drive expression of the fusion and puromycin resistant genes respectively. (FIG. 3B) Exosome surface display of fluorescent markers CD63 in living HEK293 cells, 48 h after transfection. The upper panel shows the punctuate distribution of fluorescent signals ('green/red'), indicating endosomal-lysosomal compartment distribution of the CD63 fused reporters ('yellow' arrows). In contrast, the non-fusion GFP or RFP (as control) reveals an even cytoplasm distribution (lower panel). (FIG. 3C) Mammalian expression vectors of CD9-GFP/RFP and CD81-GFP/RFP respectively. (FIG. 3D) Exosome surface display of fluorescent markers (CD9 & CD81) in HEK293 cells. For interpretation of the references to color in this figure legend, the reader is referred to our paper: Stickney et al. (2016) Development of exosome surface display technology in living human cells, Biochemical and Biophysical Research Communications 472: 53-59.

FIGS. 4A-G show according to an exemplary embodiment of the invention surface display using CD63 molecular scaffold. (FIG. 4A) Configuration of CD63 scaffold docking RFP marker to the second extra-vesicular loop. (FIG. 4B) Construction of expression vectors for CD63 fusion protein with fluorescent markers on the surface of exosomes. (FIGS. 4C-D) Fluorescent markers ('yellow' arrows) localized to intracellular vesicles of living HEK293 cell (24 h after transfection). (FIGS. 4E-G) The co-localization of displayed RFP and GFP in living HEK293 cells (72 h after transfection). For interpretation of the references to color in this figure legend, the reader is referred to our paper: Stickney et al. (2016) Development of exosome surface display technology in living human cells, Biochemical and Biophysical Research Communications 472: 53-59.

FIGS. 5A-F show according to an exemplary embodiment of the invention engineered stable cell lines express CD63-GFP and secrete surface displayed exosomes that can be taken up by recipient cells. Following the establishment of stable cell lines, images were taken from the same field to show GFP-positive cells (FIG. 5A) and the intracellular localization of GFP-positive vesicles (FIG. 5B) at 20 magnification. The screen-shots of NS300 of the GFP-negative control cells (FIG. 5C) and GFP-positive (white arrows) of the engineered stable cells (FIG. 5D). The nanoparticle tracking analysis of GFP-positive vesicles released from the engineered stable cells (FIG. 5E). The superimposed red line indicates mean±SD from 3 experiments. Two dominant peaks were recorded at ~160 nm and ~86 nm, along with minor peaks at ~284 nm, ~337 nm or <~80 nm. The concentration of the fluorescent particles used for the analysis is ~5 $10^6$/ml. (f) CD63-GFP-positive nanoparticles are shown in cells supplied with engineered exosomes (right panel), versus the control without engineered exosomes (left panel), indicating exosomes uptake by recipient cells. For interpretation of the references to color in this figure legend, the reader is referred to our paper: Stickney et al. (2016) Development of exosome surface display technology in living human cells, Biochemical and Biophysical Research Communications 472: 53-59.

FIGS. 6A-C show according to an exemplary embodiment of the invention engineering strategies of protein scaffolds. (FIG. 6A) Topology of wild-type (WT) CD63 showing an M-like membrane protein structure (FIG. 6B) Insertion of a receptor or antigen into the large loop of CD63, Deletion of the N terminus and first transmembrane domain, with the attachment of a targeting molecule to the exterior and cargo attached to the interior.

FIG. 7 shows according to an exemplary embodiment of the invention exosome surface displayed CD63-GFP localized to the endosomal compartments. Images were taken at 20× magnification at 48 hours after cotransfection of Tetraspanin-RFP and GFP-Rab5a.

DETAILED DESCRIPTION

Exosomes are lipid-bilayer-enclosed extracellular vesicles that transport signaling proteins, nucleic acids, and lipids among cells. They are actively secreted by almost all types of cells, exist in body fluids, and circulate in the blood. Although the biogenesis of exosomes remains unclear, they are believed to be derived from endosomal-lysosomal compartments. Exosomes are initially formed during the inward budding of late endosomes and subsequently stored inside of multi-vesicular body (MVB) before being released into the extracellular space. Thus, it is not surprising that members of the endosomal forming and sorting proteins (Rab5, Rab27 and Rab35), heat-shock proteins, and tetraspanins (CD9, CD63 and CD81) are enriched in exosomes.

Tetraspanins are a special class of surface proteins that transverse four times of exosome membrane. Among them, CD63 is the most abundant and is considered a hallmark of exosomes. These trans-membrane proteins contain both extra- and intra-vesicular domains making them most suitable to display molecules on the surface of exosomes. In this invention, we have explored the engineering of exosome in living human cells using CD63 as a scaffold. This invention establishes the groundwork for exosome surface engineering via tetraspanin CD63 and its family members CD9 and CD81.

Design and Construction of Tetraspanin Fusion Proteins

Figure 1A:
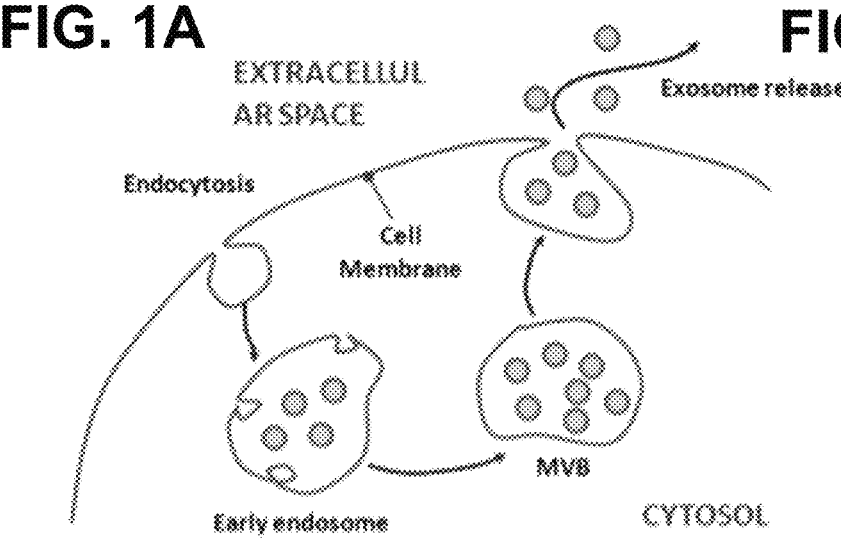
FIGS. 1A-B show according to an exemplary embodiment of the invention exosome biogenesis and composition.
Figure 1B:
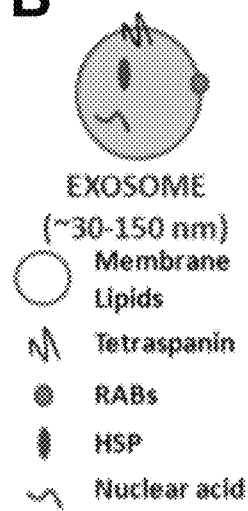
Figure 3A:
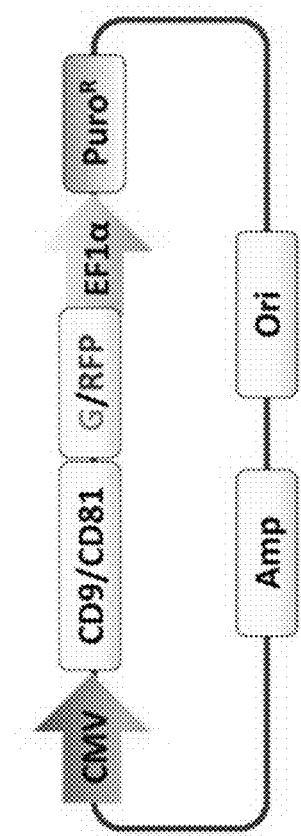
FIGS. 3A-D show according to an exemplary embodiment of the invention expression of tetraspanin chimeric proteins in mammalian cells.
Figure 3B:
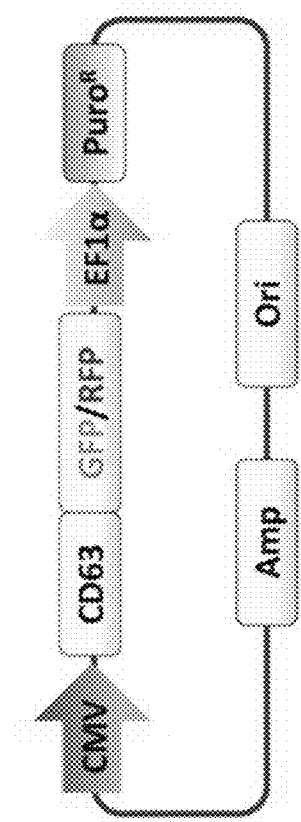
Figure 3C:
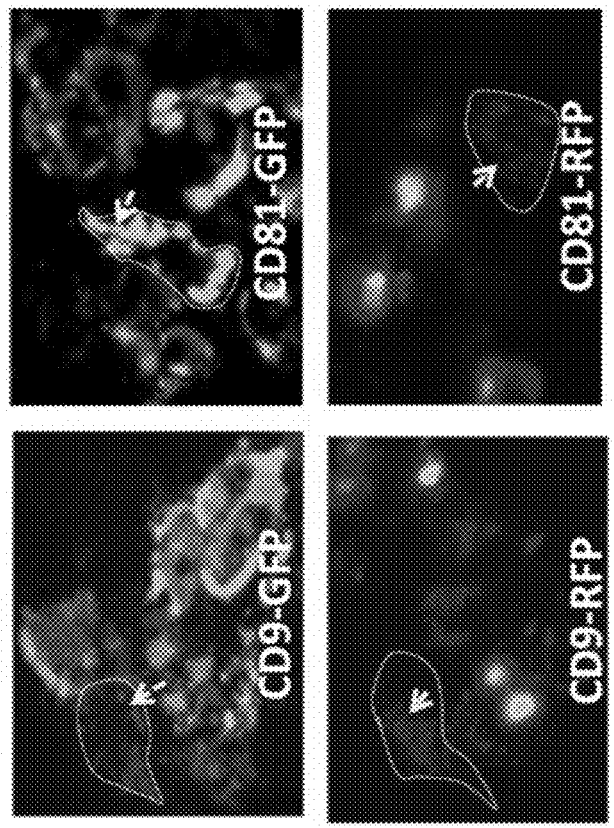

The C-terminal fusion expression vector of human tetraspanin CD63 with GFP or RFP is configured 5'→3' as follows: a constitutive cytomegalovirus (CMV) promoter, the coding sequences of the human CD63, an in frame GFP or RFP, and a poly-adenylation (Poly-A) signal. To add an antibiotics selection marker, a constitutive promoter EF1a with a puromycin resistance gene was incorporated (FIG. 3A). Similarly, two other sets of fusion proteins of CD9 and CD81 were constructed (FIG. 3C). The construction was carried out with a combination of PCR amplification of individual fragments and subsequently joined together using a seamless cloning kit (System Biosciences, Inc., Mountain View, Calif., USA). To display a RFP reporter on the outer surface of exosome, we inserted the coding sequences of RFP into the second loop of CD63 (FIG. 3A, 3B). Additionally, a GFP-Rab5a fusion protein was assembled to serve as an endosome marker. All final constructs were confirmed by DNA sequencing (ELIM BIO, Hayward, Calif.). The genetically encoded protein sequences and gene ID are provided in the Table 1 at the end of the description.

Cell Culture and Transfection

Human embryonic kidney cells (HEK293) were cultured and maintained in high glucose Dulbecco's Minimal Essential Medium (DMEM) supplemented with 10% fetal bovine serum, 2 mM GlutaMax (Life Technologies, Grand Island, N.Y., USA), 100 U/ml penicillin, and 100 U/ml streptomycin. At ~80e90% confluency, cells were passaged with 0.25% trypsin-EDTA for dissociation. All transfections were performed in 6-well plates. At 40e60% con-fluency, cells were transfected using plasmid DNA (1e2 mg/well) with PureFection Transfection Reagent (System Biosciences, Inc., Mountain View, Calif., USA) or FuGENE6 transfection reagent (Promega Corp. Madison, Wis.) according to the user manuals.

Drug Selection and Stable Cell Lines Establishment

After transfection for 48 h, HEK293 cells were switched to a culture medium containing 5 mg/ml puromycin. Stable cell lines were considered to be established when they remained GFP-positive and puromycin resistant after long period (>8 weeks) culture. Stable cell lines were maintained in complete medium under puromycin pressure and then switched to puromycin-free medium for at least two passages before conducting any experiments.

Exosome Preparation and Purification

Exosomes were obtained from the supernatant of cells as described previously with minor modification (Peterson et al. Antes, Integrated systems for exosome investigation, Methods (2015), http://dx.doi.org/10.1016/j.ymeth.2015.04.015). Briefly, stable cells were grown until 70e80% confluency. The spent medium was then replaced by fresh growth medium, and after an additional 48-h culture, the conditioned medium was collected. Following initial centrifugation for 30 min at 3000 g, 4 degrees Celsius, the collected medium was mixed with ExoQuick-TC (System Biosciences, Inc., California, USA) and subjected to another centrifugation under the same condition. The resulting pellet (exosome) was either re-suspended in a phosphate buffer solution for further analysis, or stored at 80 degrees Celsius for future use.

Nanoparticle Tracking Analysis

Exosomes isolated from the engineered and control cells were both subjected to nanoparticle tracking analysis, using NS300 (Malvern Instruments Ltd). As done in a typical experiment, the exosome samples were subject to nanoparticle tracking analysis after a 1:5 dilution. The GFP fluorescence mode was used for the specific detection of de novo labeled exosomes from the engineered stable cell lines. Data was collected from 3 experiments under the same monitoring conditions and presented as mean±SD.

Exosome Uptake Assay

Equal amounts (50 mg) of exosomes isolated from the culture medium of either engineered or parental control cells were added to the cultured HEK293 cells at confluency of 80%. After 48 h of incubation, cells were washed twice with the prewarmed PBS buffer before imaging.

Live Cell Monitoring with Microscope

Live cells were monitored using a LEICA DMI3000B fluorescent microscope. Data collection and processing was performed with LAS 3.8 software. The same field was subject to imaging under different conditions such as phase contrast, GFP and/or RFP. Imaging was further processed and merged using Adobe Photoshop CS program to illustrate the relationships of GFP and/or RFP positivity.

Results

Exosome Surface Engineering Strategy and Experiment Design

One common feature of surface display systems is the use of certain native surface proteins as molecular scaffolds. Individual organism, such as bacterial phage, yeast and liposome anchors at least one such a scaffold protein on its surface. For exosomes, the protein is tetraspanins. All tetraspanins share similar "M"-shape topology on exosomal surface, including two short intra-vesicle termini, two extra-vesicle loops, a small intra-vesicle loop and four transmembrane domains (FIG. 2A). Tetraspanins are relatively small (200-350 aa), making them particularly desirable for exosome display via molecular engineering in mammalian cells.

To achieve this goal, we constructed fluorescent reporters with both the inner and outer surface modification of tetraspanin (FIG. 2A). Using these fluorescent reporters we were able to monitor the incorporation of the tetraspanin scaffold correctly onto exosomes (FIG. 2B-C). This system will also allow us to:

(1) Establish stable cell lines for long-term study of the genesis and secretion of exosomes in living mammalian cells;

(2) Isolate and analyze the endogenous exosomes via fluorescent surface markers (FIG. 2D-E);

(3) Provide a new platform for supporting a broad future applications such as exosome biogenesis, targeted drug delivery, exosome-based therapy, proteineprotein interaction, molecular imaging, and vaccination, etc. (FIG. 2F).

Tetraspanin CD63 Scaffold Enables Surface Display of Functional Fluorescent Proteins to Endocytic Compartments We first generated a cohort of 6 chimeric proteins to test whether tetraspanins are suitable for the surface display with cultured HEK293 cells. To display a special protein to the inner surface of an exosome, we initially fused fluorescent proteins at the C-terminus of CD63 (FIG. 3A). Because CD63 contains the intrinsic membrane localization signal, we expected to see the green fluorescent light-up of endocytic vesicles/granules. As demonstrated in FIG. 3B, CD63 is able to efficiently direct the GFP or RFP to the endocytic compartment, evidenced by the punctuated granular fluorescence in the cytosol (FIG. 3B, 'yellow' arrows in upper panel). In contrast, cytosolic expression of either GFP or RFP alone revealed an even, diffused accumulation of reporters in control cells, which is consistent with their cytosolic distributions of native GPF or RFP (FIG. 2B, lower panel).

Figure 3D:
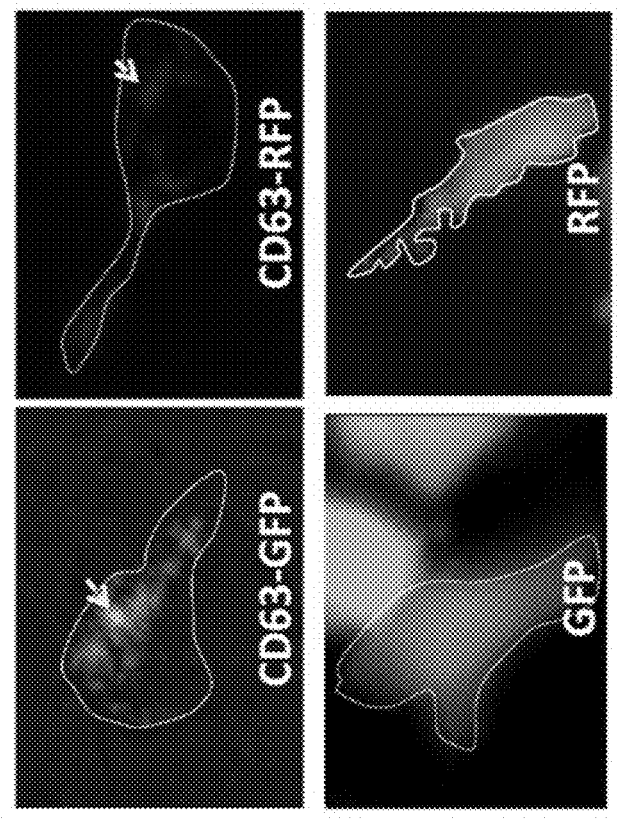

Next, we assessed whether other tetraspanins (CD9, CD81) could also be used to directly fuse reporters into the same intracellular compartment (FIG. 3C). As expected, CD9 and CD81 fusions also present distinct and granular signal within cytosol (FIG. 3D), similar to the pattern of CD63. Thus, tetraspanins in general can serve as a robust molecular scaffold to display different proteins on exosomes in cultured HEK293 cells.

Figure 7:
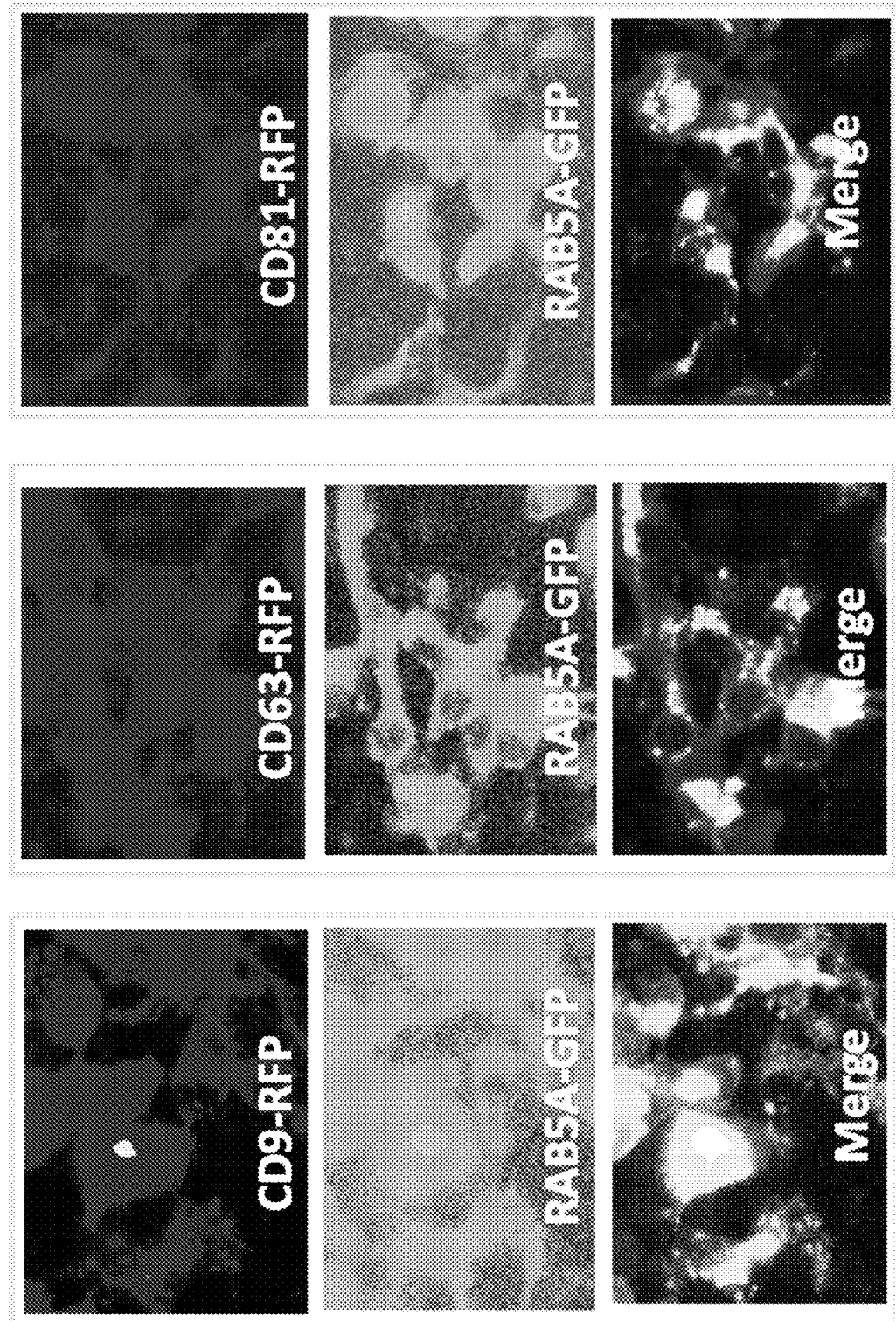

To further determine whether the displayed fluorescent markers localize to the proper endocytic compartments within living cells, we constructed an endosomal reporter by tagging GFP to a well-known endosomal protein, Rab5a. As expected, GFP-Rab5A localizes to endocytic compartments, which perfectly matched the positive sites in all three tetraspanin fusions (CD9-RFP, CD63-RFP & CD81-RFP) (FIGS. 7A-C). These results strongly support the notion that tetraspanins display proteins on the surface of exosomes that are normally situated at endocytic compartments before being released into extracellular space.

Together, our results show that tetraspanins can serve as a molecular scaffold to direct fused peptides to endocytic compartments in exosomes. The readily detectable fluorescent markers indicate that the displayed peptides are structurally and functionally preserved, and the system is robust and reliable. Since CD63 is the most abundant surface marker of exosomes, it was chosen for the further development for outer surface display.

A-S Site in Loop 2 of CD63 Enables Outer Surface Display

The two termini of CD63 molecule and the small loop between transmembrane domain 2 and 3 are situated inside of the exosome, whereas the other two loops are located outside (FIG. 4A). Of the two outside loops, the larger one (103aa) is more exposed with most antibodies developed against this region. Accordingly, we chose this loop at the site between Alanine 133 and Serine134 (we coined it "A-S site") for the surface display. This site is localized in an accessible region; away from a complicated mushroom-like structure formed by multiple disulfide bonds. Such a design will allow the displayed proteins to easily interact with the targeted cells with minimum steric hindrance.

To determine whether the displayed peptide has reserved function after insertion in this loop, we constructed the ruby-RFP-CD63 fusion protein using the A-S site. Instead of using a native CD63, we inserted RFP into our previously validated CD63-GFP and built a tri-fusion with dual fluorescent reporters (FIG. 4B). This helped us by using GFP as a positive control to monitor the correct exosomal anchoring, and simultaneously using RFP to test the remaining function when displayed in vivo. As shown in FIGS. 4C-D, the fluorescent signals lighted up vesicles or granules early (24 h after transfection). Some signals appeared more or less concentrated at certain micro-domains of vesicles, suggesting the potential focal points for inverted budding processes (yellow arrow). Longer incubation time (72 h after transfection) leads to more intense and distinct fluorescence signals, which localized to intracellular granules or multi-vesicular body (MVB)-like structures (FIG. 4E-G). The co-localization of displayed RFP and GFP support the notion that the molecular scaffold does not damage the overall structure of the fusion proteins and preserves their functions.

Stable Cells Secrete Engineered Exosomes into Culture Medium with Intact Function To confirm the observation in our transient experiments, we carried out long-term studies by establishing stable cell lines. As shown in FIGS. 5A-B, genetically transformed HEK293 cells exhibited distinct fluorescence granules in the cytoplasm. In some areas, aggregation of GFP-positive granules was apparent, suggesting the sites of MVB. These results confirm our observations from transient transfection studies and provide cellular factories for permanently producing surface displayed exosomes. Importantly, long-term survival of engineered HEK293 cells supports a notion that this novel system is suitable for both short and long term studies of exosome biogenesis. To further examine whether the engineered exosomes can mature and ultimately release into extracellular space, we isolated exosomes from the conditioned medium for nanoparticle tracking analysis. While little or no fluorescence signals are found in the control samples (FIG. 5C), CD63-GFP-positive nanoparticles are abundant as recorded by video under identical conditions (FIG. 5D), indicating that they are truly surface displayed exosomes from engineered cells. These GFP-positive particles have two major peaks at ~86 nm and ~160 nm (FIG. 5E), which is consistent with reported sizes of exosomes. Other minor peaks (~240 nm & ~300 nm) are also present; suggesting larger sized particles. Additional smaller peaks (<~80 nm) are visible albeit in small amounts (FIG. 5E). Finally, we examined the internalization process of these engineered exosomes. Internalization of exosomes occurs frequently at recipient cells via a direct fusion with the plasma membrane or endocytosis. After applying 50 mg exosomal preparation to the culture medium of stable cells and incubating for 48 h, the GFP-positive particles appeared in the cytosol of recipient cells (FIG. 5F, right panel), suggesting the uptake of engineered exosomes. In contrast, the control cells without GFP-displayed exosomes showed no GFP fluorescent background (FIG. 5F, left panel). These results indicate that surface displayed exosomes are functional and can be taken up by recipient cells as reported.

Tetraspanin Scaffold for Delivery of Bioactive Cargo

Infra the description referred to fluorescent proteins attached to tetraspanin. This section discusses tetraspanin as a delivery mechanism for bioactive cargo. Bioactive cargo that could be attached to tetraspanin is a 6×His tag for exosome purification, an imaging protein (e.g. GFP or RFP or luciferase), a viral antigen epitope, a cancer antigen epitope, a protein drug (e.g. decoy receptors, single chain antibody, suicide genes), a suicide gene, or a therapeutic protein for replacement therapy.

Generally speaking the invention pertains to embodiments of an engineered exosome for the delivery of bioactive cargo/protein. The proteins could be attached to one, two or three different attachments sites. The invention includes embodiments of an engineered exosome for the delivery of bioactive cargo with different combinations of the described cargo or attachment sites. In these embodiments, an exosome defining an inner-vesicle space and an outer-vesicle space. The exosome incorporates a tetraspanin transmembrane anchoring scaffold onto the membrane of the exosome.

(FIG. 6A) The tetraspanin transmembrane anchoring scaffold could have a first terminal attachment site in the inner-vesicle space. A first protein 610 could be attached to the C-terminal attachment site of the tetraspanin transmembrane anchoring scaffold right before the stop codon so that the first peptide is located in the inner-vesicle space.

Examples of the first peptide are: an imaging protein, a protein drug, a suicide protein, an enzyme for replacement therapy.

Figure 6A:
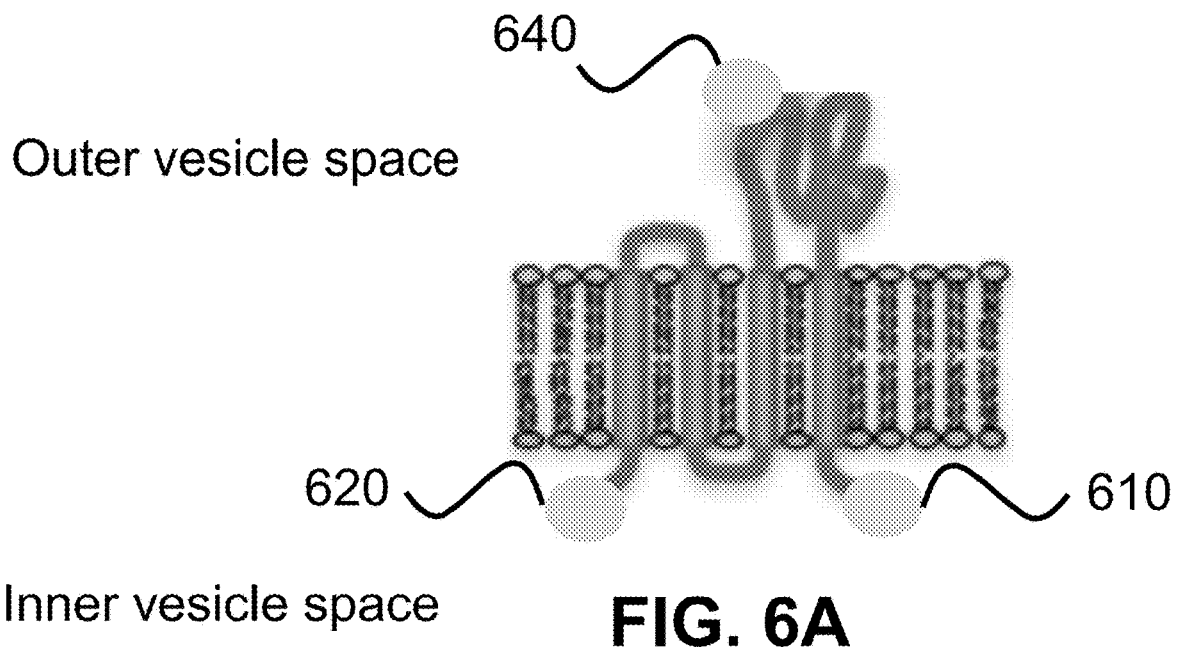
Figure 6B:
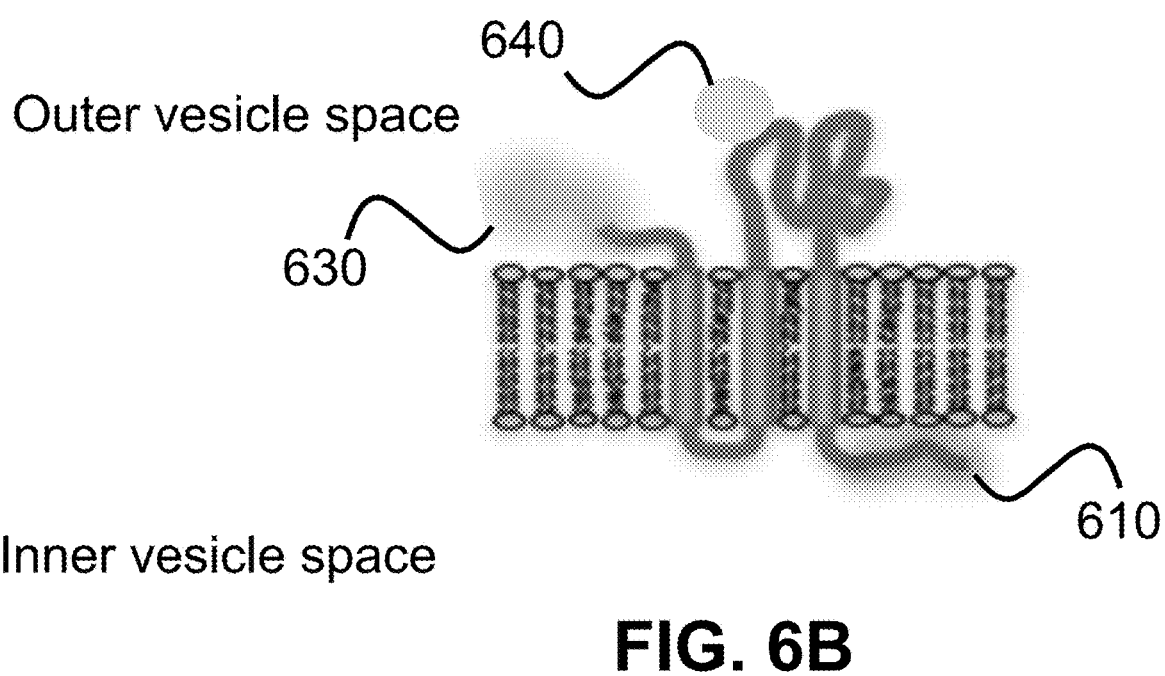

(FIG. 6A and FIG. 6B) The tetraspanin transmembrane anchoring scaffold could have a second terminal attachment site in the inner-vesicle space or in the outer-vesicle space. A second peptide could be attached to the N-terminal attachment site of the tetraspanin transmembrane anchoring scaffold so that the second peptide is located in the inner-vesicle space or in the outer-vesicle space. When the second peptide 620 is located in the inner-vesicle space a full length tetraspanin is used to serve as the scaffold and the peptide is inserted immediately after the start codon; the second terminal attachment site is the N-terminus of the tetraspanin (FIG. 6A). When the second peptide 630 is located in the outer-vesicle space a truncated tetraspanin is used to serve as the scaffold; the second terminal attachment site is the N-terminus of the tetraspanin (FIG. 6B).

Examples of the second peptide are: a 6×His tag for detection and purification, an imaging protein, a viral antigen epitope, a cancer antigen epitope, a single chain antibody, or a protein drug.

(FIG. 6A and FIG. 6B) The tetraspanin transmembrane anchoring scaffold could have a loop attachment site in the outer-vesicle space. A third peptide 640 could be attached to the loop attachment site of the tetraspanin transmembrane anchoring scaffold so that the third peptide 640 is located in the outer-vesicle space.

Examples of the third peptide are: an imaging protein, a viral antigen epitope, a cancer antigen epitope, a protein drug, a suicide gene, a receptor for active biomolecules, or a therapeutic protein for replacement therapy.

SEQUENCES
Note: protein sequences of Tetraspanins or Rab5a are underlined whereas fluorescent reporters and their linker sequences are bold highlighted.
SEQ ID 1
CD63-GFG, 496 aa
MAVEGGMKCVKFLLYVLLLAFCACAVGLIAVGVGAQLVLSQTIIQGATP

GSLLPVVIIAVGVFLFLVAFVGCCGACKENYCLMITFAIFLSLIMLVEVA

AAIAGYVFRDKVMSEFNNNFRQQMENYPKNNHTASILDRMQADFKCCGA

ANYTDWEKIPSMSKNRVPDSCCINVTVGCGINFNEKAIHKEGCVEKIGGW

LRKNVLVVAAAALGIAFVEVLGIVFACCLVKSIRSGYEVMMESDESGLP

AMEIECRITGTLNGVEFELVGGGEGTPKQGRMTNKMKSTKGALTFS

PYLLSHVMGYGFYHFGTYPSGYENPFLHAINNGGYTNTRIEKYEDGG

VLHVSFSYRYEAGRVIGDFKVVGTGFPEDSVIFTDKIIRSNATVEHLHP

MGDNVLVGSFARTFSLRDGGYYSFVVDSHMHFKSAIHPSILQNGGPM

FAFRRVEELHSNTELGIVEYQHAFKTPIAFARSRAQSSNSAVDGTAGP

GSTGSRHHHHHH

SEQ ID 2
CD63-RFP, 477 aa
MAVEGGMKCVKFLLYVLLLAFCACAVGLIAVGVGAQLVLSQTIIQGATP

GSLLPVVIIAVGVFLFLVAFVGCCGACKENYCLMITFAIFLSLIMLVEVA

AAIAGYVERDKVMSEFNNNFRQQMENYPKNNHTASILDRMQADFKCCGA

ANYTDWEKIPSMSKNRVPDSCCINVTVGCGINFNEKAIHKEGCVEKIGGW

LRKNVLVVAAAALGIAFVEVLGIVFACCLVKSIRSGYEVMMGKLTMASS

EDVIKEFMRFKVKMEGSVNGHEFEIEGEGEGRPYEGTQTAKLKVTK

GGPLPFSWDILSPQFQYGSKAYVKHPADIPDYLKLSFPEGFKWERFM

NFEDGGVVTVTQDSTLQDGEFIYKVKLRGTNFPSDGPVMQKKTMGW

EASTERMYPEDGALKGEIKMRLKLKDGGHYDAEVKTTYKAKKQVQ

LPGAYMTDIKLDIISHNGDYTIVEQYERAEGRHSTGAGSIIRSIII

SEQ ID 3
CD9-GFP, 486 aa
MPVKGGTKCIKYLLFGFNFIFWLAGIAVLAIGLWLRFDSQTKSIFEQETN

NNNSSFYTGVYILIGAGALMMLVGFLGCCGAVQESQCMLGLFFGFLLVIF

AIEIAAAIWGYSHKDEVIKEVQEFYKDTYNKLKTKDEPQRETLKAIHYAL

NCCGLAGGVEQFISDICPKKDVLETFTVKSCPDAIKEVFDNKFHIIGAVG

IGIAVVMIFGMIFSMILCCAIRRNREMVMESDESGLPAMEIECRITGTLN

GVEFELVGGGEGTPKQGRMTNKMKSTKGALTFSPYLLSHVMGYGFYHF

GTYPSGYENPFLHAINNGGYTNTRIEKYEDGGVLHVSFSYRYEAGRVI

GDFKVVGTGFPEDSVIFTDKIIRSNATVEHLHPMGDNVLVGSFARTFS

LRDGGYYSFVVDSHMHFKSAIHPSILQNGGPMFAFRRVEELHSNTEL

GIVEYQHAFKTPIAFARSRAQSSNSAVDGTAGPGSTGSRHHHHHH

SEQ ID 4
CD9-RFP, 467 aa
MPVKGGTKCIKYLLFGFNFIFWLAGIAVLAIGLWLRFDSQTKSIFEQETN

NNNSSFYTGVYILIGAGALMMLVGFLGCCGAVQESQCMLGLFFGFLLVIF

AIEIAAAIWGYSHKDEVIKEVQEFYKDTYNKLKTKDEPQRETLKAIHYAL

NCCGLAGGVEQFISDICPKKDVLETFTVKSCPDAIKEVFDNKFHIIGAVG

IGIAVVMIFGMIFSMILCCAIRRNREMVMGKLTMASSEDVIKEFMRFKVK

MEGSVNGHEFEIEGEGEGRPYEGTQTAKLKVTKGGPLPFSWDILSPQF

QYGSKAYVKHPADIPDYLKLSFPEGFKWERFMNFEDGGVVTVTQDS

TLQDGEFIYKVKLRGTNFPSDGPVMQKKTMGWEASTERMYPEDGAL

KGEIKMRLKLKDGGHYDAEVKTTYKAKKQVQLPGAYMTDIKLDIIS

HNGDYTIVEQYERAEGRHSTGAGSIIRSIII

SEQ ID 5
CD81-GFP, 494 aa
MGVEGCTKCIKYLLFVFNFVFWLAGGVILGVALWLRHDPQTTNLLYLEL

GDKPAPNTFYVGIYILIAVGAVMMFVGFLGCYGAIQESQCLLGTFFTCLV

ILFACEVAAGIWGFVNKDQIAKDVKQFYDQALQQAVVDDDANNAKAVV

KTFHETLDCCGSSTLTALTTSVLKNNLCPSGSNIISNLFKEDCHQKIDDL

FSGKLYLIGIAAIVVAVIMIFEMILSMVLCCGIRNSSVYMESDESGLPAM

EIECRITGTLNGVEFELVGGGEGTPKQGRMTNKMKSTKGALTFSPYLLS

HVMGYGFYHFGTYPSGYENPFLHAINNGGYTNTRIEKYEDGGVLHVS

FSYRYEAGRVIGDFKVVGTGFPEDSVIFTDKIIRSNATVEHLPMGDN

VLVGSFARTFSLRDGGYYSFVVDSHMHFKSAIHPSILQNGGPMFAFRR

VEELHSNTELGIVEYQHAFKTPIAFARSRAQSSNSAVDGTAGPGSTGS

RHHHHHH

SEQ ID 6
CD81-RFP, 475 aa
MGVEGCTKCIKYLLFVFNFVFWLAGGVILGVALWLRHDPQTTNLLYLEL

GDKPAPNTFYVGIYILIAVGAVMMFVGFLGCYGAIQESQCLLGTFFTCLV

ILFACEVAAGIWGFVNKDQIAKDVKQFYDQALQQAVVDDDANNAKAVV

KTFHETLDCCGSSTLTALTTSVLKNNLCPSGSNIISNLFKEDCHQKIDDL

FSGKLYLIGIAAIVVAVIMIFEMILSMVLCCGIRNSSVYMGKLTMASSED

VIKEFMRFKVKMEGSVNGHEFEIEGEGEGRPYEGTQTAKLKVTKGGPL

PFSWDILSPQFQYGSKAYVKHPADIPDYLKLSFPEGFKWERFMNFED

GGVVTVTQDSTLQDGEFIYKVKLRGTNFPSDGPVMQKKTMGWEAST

ERMYPEDGALKGEIKMRLKLKDGGHYDAEVKTTYKAKKQVQLPGA

YMTDIKLDIISHNGDYTIVEQYERAEGRHSTGAGSIIRSIII

SEQ ID 7
Nter-CD63-RFP-Cter-CD63-GFP, 754 aa
MAVEGGMKCVKFLLYVLLLAFCACAVGLIAVGVGAQLVLSQTIIQGATP

GSLLPVVIIAVGVFLFLVAFVGCCGACKENYCLMITFAIFLSLIMLVEVA

AAIAGYVFRDKVMSEFNNNFRQQMENYPKNNHTAFEDMGKLTMASSED

VIKEFMRFKVKMEGSVNGHEFEIEGEGEGRPYEGTQTAKLKVTKGG

PLPFSWDILSPQFQYGSKAYVKHPADIPDYLKLSFPEGFKWERFMNFE

DGGVVTVTQDSTLQDGEFIYKVKLRGTNFPSDGPVMQKKTMGWEAS

TERMYPEDGALKGEIKMRLKLKDGGHYDAEVKTTYKAKKQVQLPG

AYMTDIKLDIISHNGDYTIVEQYERAEGRHSTGAGSIIRSIIIHHHHHHI

-continued

AAAPGLDLNSILDRMQADFKCCGAANYTDWEKIPSMSKNRVPDSCCINV

TVGCGINFNEKAIHKEGCVEKIGGWLRKNVLVVAAAALGIAFVEVLGIVF

ACCLVKSIRSGYEVMMESDESGLPAMEIECRITGTLNGVEFELVGGGE

GTPKQGRMTNKMKSTKGALTFSPYLLSHVMGYGFYHFGTYPSGYEN

PFLHAINNGGYTNTRIEKYEDGGVLHVSFSYRYEAGRVIGDFKVVGT

GFPEDSVIFTDKIIRSNATVEHLHPMGDNVLVGSFARTFSLRDGGYYS

FVVDSHMHFKSAIHPSILQNGGPMFAFRRVEELHSNTELGIVEYQHAF

KTPIAFARSRAQSSNSAVDGTAGPGSTGSRHHHHHH

SEQ ID 8
GFP-RAB5A, 473 aa
MESDESGLPAMEIECRITGTLNGVEFELVGGGEGTPKQGRMTNKMK

STKGALTFSPYLLSHVMGYGFYHFGTYPSGYENPFLHAINNGGYTNT

RIEKYEDGGVLHVSFSYRYEAGRVIGDFKVVGTGFPEDSVIFTDKIIRS

NATVEHLHPMGDNVLVGSFARTFSLRDGGYYSFVVDSHMHFKSAIHP

-continued

SILQNGGPMFAFRRVEELHSNTELGIVEYQHAFKTPIAFARSRAQSSNS

AVDGTAGPGSTGSRSRASEFMASRGATRPNGPNTGNKICQFKLVLLGES

AVGKSSLVLRFVKGQFHEFQESTIGAAFLTQTVCLDDTTVKFEIWDTAGQ

ERYHSLAPMYYRGAQAAIVVYDITNEESFARAKNWVKELQRQASPNIVIA

LSGNKADLANKRAVDFQEAQSYADDNSLLFMETSAKTSMNVNEIFMAIA

KKLPKNEPQNPGANSARGRGVDLTEPTQPTRNQCCSN

TABLE 1

Gene IDs of fusion proteins

| Human Protein | Gene ID |
| --- | --- |
| CD63 | 91199544 |
| CD9 | 319738657 |
| CD81 | 62240999 |
| GFP-Rab5a | 19923262 |

What is claimed is:

1. An engineered exosome for the delivery of bioactive cargo, comprising:
   an exosome defining an inner-vesicle space and an outer-vesicle space, wherein the exosome incorporates a tetraspanin transmembrane anchoring scaffold onto the membrane of the exosome,
   wherein the tetraspanin transmembrane anchoring scaffold has a C-terminal attachment site in the inner-vesicle space,
   wherein the tetraspanin transmembrane anchoring scaffold has a N-terminal attachment site in the inner-vesicle space or the outer-vesicle space, and
   wherein the tetraspanin transmembrane anchoring scaffold has a loop attachment site in the outer-vesicle space,
   wherein a first peptide is attached to the C-terminal attachment site of the tetraspanin transmembrane anchoring scaffold so that the first peptide is located in the inner-vesicle space,
   wherein a second peptide is attached to the N-terminal attachment site of the tetraspanin transmembrane anchoring scaffold so that the second peptide is located in the inner-vesicle space or in the outer-vesicle space,
   wherein a third peptide is attached to the loop attachment site of the tetraspanin transmembrane anchoring scaffold so that the third peptide is located in the outer-vesicle space; and
   wherein the tetraspanin transmembrane anchoring scaffold originate from proteins CD63, CD9 and/or CD81.

2. The engineered exosome as set forth in claim 1, wherein the second peptide is attached to the second terminal attachment site of the tetraspanin transmembrane anchoring scaffold so that the second peptide is located in the inner-vesicle space, wherein a full length tetraspanin serves as the scaffold, and wherein the second terminal attachment site is the N-terminus of the tetraspanin.

3. The engineered exosome as set forth in claim 1, wherein the second peptide is attached to the second terminal attachment site of the tetraspanin transmembrane anchoring scaffold so that the second peptide is located in the outer-vesicle space, wherein a truncated tetraspanin serves as the scaffold, and wherein the second terminal attachment site is the N-terminus of the tetraspanin.

4. The engineered exosome as set forth in claim 1, wherein the first peptide is an imaging protein, a protein drug, a suicide protein, an enzyme for replacement therapy.

5. The engineered exosome as set forth in claim 1, wherein the second peptide is a 6xHis tag for detection and purification, an imaging protein, a viral antigen epitope, a cancer antigen epitope, a single chain antibody, or protein drug.

6. The engineered exosome as set forth in claim 1, wherein the third peptide is an imaging protein, a viral antigen epitope, a cancer antigen epitope, a protein drug, a suicide gene, a receptor for active biomolecules, or a therapeutic protein for replacement therapy.

* * * * *

SEQUENCE LISTING

<160> NUMBER OF SEQ ID NOS: 8

<210> SEQ ID NO 1
<211> LENGTH: 496
<212> TYPE: PRT
<213> ORGANISM: Homo sapiens

<400> SEQUENCE: 1

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Asn Val Thr Val Gly
                165                 170                 175

Cys Gly Ile Asn Phe Asn Glu Lys Ala Ile His Lys Glu Gly Cys Val
            180                 185                 190

Glu Lys Ile Gly Gly Trp Leu Arg Lys Asn Val Leu Val Val Ala Ala
        195                 200                 205

Ala Ala Leu Gly Ile Ala Phe Val Glu Val Leu Gly Ile Val Phe Ala

```
                    210                 215                 220
Cys Cys Leu Val Lys Ser Ile Arg Ser Gly Tyr Glu Val Met Met Glu
225                 230                 235                 240

Ser Asp Glu Ser Gly Leu Pro Ala Met Glu Ile Glu Cys Arg Ile Thr
                245                 250                 255

Gly Thr Leu Asn Gly Val Glu Phe Glu Leu Val Gly Gly Glu Gly
                260                 265                 270

Thr Pro Lys Gln Gly Arg Met Thr Asn Lys Met Lys Ser Thr Lys Gly
                275                 280                 285

Ala Leu Thr Phe Ser Pro Tyr Leu Leu Ser His Val Met Gly Tyr Gly
                290                 295                 300

Phe Tyr His Phe Gly Thr Tyr Pro Ser Gly Tyr Glu Asn Pro Phe Leu
305                 310                 315                 320

His Ala Ile Asn Asn Gly Gly Tyr Thr Asn Thr Arg Ile Glu Lys Tyr
                325                 330                 335

Glu Asp Gly Gly Val Leu His Val Ser Phe Ser Tyr Arg Tyr Glu Ala
                340                 345                 350

Gly Arg Val Ile Gly Asp Phe Lys Val Val Gly Thr Gly Phe Pro Glu
                355                 360                 365

Asp Ser Val Ile Phe Thr Asp Lys Ile Ile Arg Ser Asn Ala Thr Val
370                 375                 380

Glu His Leu His Pro Met Gly Asp Asn Val Leu Val Gly Ser Phe Ala
385                 390                 395                 400

Arg Thr Phe Ser Leu Arg Asp Gly Gly Tyr Tyr Ser Phe Val Val Asp
                405                 410                 415

Ser His Met His Phe Lys Ser Ala Ile His Pro Ser Ile Leu Gln Asn
                420                 425                 430

Gly Gly Pro Met Phe Ala Phe Arg Arg Val Glu Glu Leu His Ser Asn
                435                 440                 445

Thr Glu Leu Gly Ile Val Glu Tyr Gln His Ala Phe Lys Thr Pro Ile
                450                 455                 460

Ala Phe Ala Arg Ser Arg Ala Gln Ser Ser Asn Ser Ala Val Asp Gly
465                 470                 475                 480

Thr Ala Gly Pro Gly Ser Thr Gly Ser Arg His His His His His His
                485                 490                 495

<210> SEQ ID NO 2
<211> LENGTH: 477
<212> TYPE: PRT
<213> ORGANISM: Homo sapiens

<400> SEQUENCE: 2

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
                20                  25                  30

Val Gly Ala Gln Leu Val Leu Ser Gln Thr Ile Ile Gln Gly Ala Thr
                35                  40                  45

Pro Gly Ser Leu Leu Pro Val Val Ile Ala Val Gly Val Phe Leu
50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95
```

-continued

Glu Val Ala Ala Ala Ile Ala Gly Tyr Val Phe Arg Asp Lys Val Met
                100                 105                 110

Ser Glu Phe Asn Asn Phe Arg Gln Gln Met Glu Asn Tyr Pro Lys
    115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Asn Val Thr Val Gly
                165                 170                 175

Cys Gly Ile Asn Phe Asn Glu Lys Ala Ile His Lys Glu Gly Cys Val
                180                 185                 190

Glu Lys Ile Gly Gly Trp Leu Arg Lys Asn Val Leu Val Ala Ala
    195                 200                 205

Ala Ala Leu Gly Ile Ala Phe Val Glu Val Leu Gly Ile Val Phe Ala
210                 215                 220

Cys Cys Leu Val Lys Ser Ile Arg Ser Gly Tyr Glu Val Met Met Gly
225                 230                 235                 240

Lys Leu Thr Met Ala Ser Ser Glu Asp Val Ile Lys Glu Phe Met Arg
                245                 250                 255

Phe Lys Val Lys Met Glu Gly Ser Val Asn Gly His Glu Phe Glu Ile
                260                 265                 270

Glu Gly Glu Gly Glu Gly Arg Pro Tyr Glu Gly Thr Gln Thr Ala Lys
                275                 280                 285

Leu Lys Val Thr Lys Gly Gly Pro Leu Pro Phe Ser Trp Asp Ile Leu
    290                 295                 300

Ser Pro Gln Phe Gln Tyr Gly Ser Lys Ala Tyr Val Lys His Pro Ala
305                 310                 315                 320

Asp Ile Pro Asp Tyr Leu Lys Leu Ser Phe Pro Glu Gly Phe Lys Trp
                325                 330                 335

Glu Arg Phe Met Asn Phe Glu Asp Gly Gly Val Val Thr Val Thr Gln
                340                 345                 350

Asp Ser Thr Leu Gln Asp Gly Glu Phe Ile Tyr Lys Val Lys Leu Arg
                355                 360                 365

Gly Thr Asn Phe Pro Ser Asp Gly Pro Val Met Gln Lys Lys Thr Met
    370                 375                 380

Gly Trp Glu Ala Ser Thr Glu Arg Met Tyr Pro Glu Asp Gly Ala Leu
385                 390                 395                 400

Lys Gly Glu Ile Lys Met Arg Leu Lys Leu Lys Asp Gly Gly His Tyr
                405                 410                 415

Asp Ala Glu Val Lys Thr Thr Tyr Lys Ala Lys Lys Gln Val Gln Leu
                420                 425                 430

Pro Gly Ala Tyr Met Thr Asp Ile Lys Leu Asp Ile Ile Ser His Asn
    435                 440                 445

Gly Asp Tyr Thr Ile Val Glu Gln Tyr Glu Arg Ala Glu Gly Arg His
                450                 455                 460

Ser Thr Gly Ala Gly Ser Ile Ile Arg Ser Ile Ile Ile
465                 470                 475

<210> SEQ ID NO 3
<211> LENGTH: 486
<212> TYPE: PRT
<213> ORGANISM: Homo sapiens

<400> SEQUENCE: 3

```
Met Pro Val Lys Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
                20                  25                  30

Leu Trp Leu Arg Phe Asp Ser Gln Thr Lys Ser Ile Phe Glu Gln Glu
            35                  40                  45

Thr Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
                85                  90                  95

Leu Val Ile Phe Ala Ile Glu Ile Ala Ala Ala Ile Trp Gly Tyr Ser
                100                 105                 110

His Lys Asp Glu Val Ile Lys Glu Val Gln Glu Phe Tyr Lys Asp Thr
                115                 120                 125

Tyr Asn Lys Leu Lys Thr Lys Asp Glu Pro Gln Arg Glu Thr Leu Lys
    130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                165                 170                 175

Thr Val Lys Ser Cys Pro Asp Ala Ile Lys Glu Val Phe Asp Asn Lys
                180                 185                 190

Phe His Ile Ile Gly Ala Val Gly Ile Gly Ile Ala Val Val Met Ile
                195                 200                 205

Phe Gly Met Ile Phe Ser Met Ile Leu Cys Cys Ala Ile Arg Arg Asn
    210                 215                 220

Arg Glu Met Val Met Glu Ser Asp Ser Gly Leu Pro Ala Met Glu
225                 230                 235                 240

Ile Glu Cys Arg Ile Thr Gly Thr Leu Asn Gly Val Glu Phe Glu Leu
                245                 250                 255

Val Gly Gly Gly Glu Gly Thr Pro Lys Gln Gly Arg Met Thr Asn Lys
                260                 265                 270

Met Lys Ser Thr Lys Gly Ala Leu Thr Phe Ser Pro Tyr Leu Leu Ser
    275                 280                 285

His Val Met Gly Tyr Gly Phe Tyr His Phe Gly Thr Tyr Pro Ser Gly
    290                 295                 300

Tyr Glu Asn Pro Phe Leu His Ala Ile Asn Asn Gly Gly Tyr Thr Asn
305                 310                 315                 320

Thr Arg Ile Glu Lys Tyr Glu Asp Gly Gly Val Leu His Val Ser Phe
                325                 330                 335

Ser Tyr Arg Tyr Glu Ala Gly Arg Val Ile Gly Asp Phe Lys Val Val
            340                 345                 350

Gly Thr Gly Phe Pro Glu Asp Ser Val Ile Phe Thr Asp Lys Ile Ile
        355                 360                 365

Arg Ser Asn Ala Thr Val Glu His Leu His Pro Met Gly Asp Asn Val
370                 375                 380

Leu Val Gly Ser Phe Ala Arg Thr Phe Ser Leu Arg Asp Gly Gly Tyr
385                 390                 395                 400

Tyr Ser Phe Val Val Asp Ser His Met His Phe Lys Ser Ala Ile His
                405                 410                 415
```

-continued

```
Pro Ser Ile Leu Gln Asn Gly Gly Pro Met Phe Ala Phe Arg Arg Val
            420                 425                 430

Glu Glu Leu His Ser Asn Thr Glu Leu Gly Ile Val Glu Tyr Gln His
        435                 440                 445

Ala Phe Lys Thr Pro Ile Ala Phe Ala Arg Ser Arg Ala Gln Ser Ser
    450                 455                 460

Asn Ser Ala Val Asp Gly Thr Ala Gly Pro Gly Ser Thr Gly Ser Arg
465                 470                 475                 480

His His His His His His
            485

<210> SEQ ID NO 4
<211> LENGTH: 467
<212> TYPE: PRT
<213> ORGANISM: Homo sapiens

<400> SEQUENCE: 4

Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Thr Asn Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
                85                  90                  95

Leu Val Ile Phe Ala Ile Glu Ile Ala Ala Ala Ile Trp Gly Tyr Ser
            100                 105                 110

His Lys Asp Glu Val Ile Lys Glu Val Gln Glu Phe Tyr Lys Asp Thr
        115                 120                 125

Tyr Asn Lys Leu Lys Thr Lys Asp Glu Pro Gln Arg Glu Thr Leu Lys
    130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                165                 170                 175

Thr Val Lys Ser Cys Pro Asp Ala Ile Lys Glu Val Phe Asp Asn Lys
            180                 185                 190

Phe His Ile Ile Gly Ala Val Gly Ile Gly Ile Ala Val Val Met Ile
        195                 200                 205

Phe Gly Met Ile Phe Ser Met Ile Leu Cys Cys Ala Ile Arg Arg Asn
    210                 215                 220

Arg Glu Met Val Met Gly Lys Leu Thr Met Ala Ser Ser Glu Asp Val
225                 230                 235                 240

Ile Lys Glu Phe Met Arg Phe Lys Val Lys Met Glu Gly Ser Val Asn
                245                 250                 255

Gly His Glu Phe Glu Ile Glu Gly Glu Gly Gly Arg Pro Tyr Glu
            260                 265                 270

Gly Thr Gln Thr Ala Lys Leu Lys Val Thr Lys Gly Gly Pro Leu Pro
        275                 280                 285

Phe Ser Trp Asp Ile Leu Ser Pro Gln Phe Gln Tyr Gly Ser Lys Ala
    290                 295                 300
```

-continued

Tyr Val Lys His Pro Ala Asp Ile Pro Asp Tyr Leu Lys Leu Ser Phe
305                 310                 315                 320

Pro Glu Gly Phe Lys Trp Glu Arg Phe Met Asn Phe Glu Asp Gly Gly
            325                 330                 335

Val Val Thr Val Thr Gln Asp Ser Thr Leu Gln Asp Gly Glu Phe Ile
        340                 345                 350

Tyr Lys Val Lys Leu Arg Gly Thr Asn Phe Pro Ser Asp Gly Pro Val
    355                 360                 365

Met Gln Lys Lys Thr Met Gly Trp Glu Ala Ser Thr Glu Arg Met Tyr
370                 375                 380

Pro Glu Asp Gly Ala Leu Lys Gly Glu Ile Lys Met Arg Leu Lys Leu
385                 390                 395                 400

Lys Asp Gly Gly His Tyr Asp Ala Glu Val Lys Thr Thr Tyr Lys Ala
                405                 410                 415

Lys Lys Gln Val Gln Leu Pro Gly Ala Tyr Met Thr Asp Ile Lys Leu
            420                 425                 430

Asp Ile Ile Ser His Asn Gly Asp Tyr Thr Ile Val Glu Gln Tyr Glu
            435                 440                 445

Arg Ala Glu Gly Arg His Ser Thr Gly Ala Gly Ser Ile Ile Arg Ser
450                 455                 460

Ile Ile Ile
465

<210> SEQ ID NO 5
<211> LENGTH: 494
<212> TYPE: PRT
<213> ORGANISM: Homo sapiens

<400> SEQUENCE: 5

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Asn Leu Leu Tyr Leu Glu
        35                  40                  45

Leu Gly Asp Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Val Asp Asp Ala Asn Asn Ala Lys
    130                 135                 140

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala 195                 200                 205
Ala Ile Val Val Ala Val Ile Met Ile Phe Glu Met Ile Leu Ser Met
            210                 215                 220

Val Leu Cys Cys Gly Ile Arg Asn Ser Ser Val Tyr Met Glu Ser Asp
225                 230                 235                 240

Glu Ser Gly Leu Pro Ala Met Glu Ile Glu Cys Arg Ile Thr Gly Thr
                245                 250                 255

Leu Asn Gly Val Glu Phe Glu Leu Val Gly Gly Glu Gly Thr Pro
            260                 265                 270

Lys Gln Gly Arg Met Thr Asn Lys Met Lys Ser Thr Lys Gly Ala Leu
                275                 280                 285

Thr Phe Ser Pro Tyr Leu Leu Ser His Val Met Gly Tyr Gly Phe Tyr
            290                 295                 300

His Phe Gly Thr Tyr Pro Ser Gly Tyr Glu Asn Pro Phe Leu His Ala
305                 310                 315                 320

Ile Asn Asn Gly Gly Tyr Thr Asn Thr Arg Ile Glu Lys Tyr Glu Asp
                325                 330                 335

Gly Gly Val Leu His Val Ser Phe Ser Tyr Arg Tyr Glu Ala Gly Arg
            340                 345                 350

Val Ile Gly Asp Phe Lys Val Gly Thr Gly Phe Pro Glu Asp Ser
                355                 360                 365

Val Ile Phe Thr Asp Lys Ile Ile Arg Ser Asn Ala Thr Val Glu His
            370                 375                 380

Leu His Pro Met Gly Asp Asn Val Leu Val Gly Ser Phe Ala Arg Thr
385                 390                 395                 400

Phe Ser Leu Arg Asp Gly Gly Tyr Tyr Ser Phe Val Val Asp Ser His
                405                 410                 415

Met His Phe Lys Ser Ala Ile His Pro Ser Ile Leu Gln Asn Gly Gly
            420                 425                 430

Pro Met Phe Ala Phe Arg Arg Val Glu Glu Leu His Ser Asn Thr Glu
                435                 440                 445

Leu Gly Ile Val Glu Tyr Gln His Ala Phe Lys Thr Pro Ile Ala Phe
            450                 455                 460

Ala Arg Ser Arg Ala Gln Ser Ser Asn Ser Ala Val Asp Gly Thr Ala
465                 470                 475                 480

Gly Pro Gly Ser Thr Gly Ser Arg His His His His His
                485                 490

<210> SEQ ID NO 6
<211> LENGTH: 475
<212> TYPE: PRT
<213> ORGANISM: Homo sapiens

<400> SEQUENCE: 6

Met Gly Val Glu Gly Cys Thr Lys Cys Ile Lys Tyr Leu Leu Phe Val
1               5                   10                  15

Phe Asn Phe Val Phe Trp Leu Ala Gly Val Ile Leu Gly Val Ala
            20                  25                  30

Leu Trp Leu Arg His Asp Pro Gln Thr Thr Asn Leu Leu Tyr Leu Glu
            35                  40                  45

Leu Gly Asp Lys Pro Ala Pro Asn Thr Phe Tyr Val Gly Ile Tyr Ile
            50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Gly Thr Phe Phe Thr
                85                  90                  95

Cys Leu Val Ile Leu Phe Ala Cys Glu Val Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Val Asp Asp Ala Asn Asn Ala Lys
130                 135                 140

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
210                 215                 220

Val Leu Cys Cys Gly Ile Arg Asn Ser Ser Val Tyr Met Gly Lys Leu
225                 230                 235                 240

Thr Met Ala Ser Ser Glu Asp Val Ile Lys Glu Phe Met Arg Phe Lys
                245                 250                 255

Val Lys Met Glu Gly Ser Val Asn Gly His Glu Phe Glu Ile Glu Gly
            260                 265                 270

Glu Gly Glu Gly Arg Pro Tyr Glu Gly Thr Gln Thr Ala Lys Leu Lys
        275                 280                 285

Val Thr Lys Gly Gly Pro Leu Pro Phe Ser Trp Asp Ile Leu Ser Pro
290                 295                 300

Gln Phe Gln Tyr Gly Ser Lys Ala Tyr Val Lys His Pro Ala Asp Ile
305                 310                 315                 320

Pro Asp Tyr Leu Lys Leu Ser Phe Pro Glu Gly Phe Lys Trp Glu Arg
                325                 330                 335

Phe Met Asn Phe Glu Asp Gly Gly Val Val Thr Val Thr Gln Asp Ser
            340                 345                 350

Thr Leu Gln Asp Gly Glu Phe Ile Tyr Lys Val Lys Leu Arg Gly Thr
        355                 360                 365

Asn Phe Pro Ser Asp Gly Pro Val Met Gln Lys Lys Thr Met Gly Trp
370                 375                 380

Glu Ala Ser Thr Glu Arg Met Tyr Pro Glu Asp Gly Ala Leu Lys Gly
385                 390                 395                 400

Glu Ile Lys Met Arg Leu Lys Leu Lys Asp Gly Gly His Tyr Asp Ala
                405                 410                 415

Glu Val Lys Thr Thr Tyr Lys Ala Lys Lys Gln Val Gln Leu Pro Gly
            420                 425                 430

Ala Tyr Met Thr Asp Ile Lys Leu Asp Ile Ser His Asn Gly Asp
        435                 440                 445

Tyr Thr Ile Val Glu Gln Tyr Glu Arg Ala Glu Gly Arg His Ser Thr
450                 455                 460

Gly Ala Gly Ser Ile Ile Arg Ser Ile Ile Ile
465                 470                 475

<210> SEQ ID NO 7
<211> LENGTH: 754
<212> TYPE: PRT

-continued

<213> ORGANISM: Homo sapiens

<400> SEQUENCE: 7

Met Ala Val Glu Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
                100                 105                 110

Ser Glu Phe Asn Asn Asn Phe Arg Gln Gln Met Glu Asn Tyr Pro Lys
            115                 120                 125

Asn Asn His Thr Ala Phe Glu Asp Met Gly Lys Leu Thr Met Ala Ser
    130                 135                 140

Ser Glu Asp Val Ile Lys Glu Phe Met Arg Phe Lys Val Lys Met Glu
145                 150                 155                 160

Gly Ser Val Asn Gly His Glu Phe Glu Ile Glu Gly Glu Gly Glu Gly
                165                 170                 175

Arg Pro Tyr Glu Gly Thr Gln Thr Ala Lys Leu Lys Val Thr Lys Gly
            180                 185                 190

Gly Pro Leu Pro Phe Ser Trp Asp Ile Leu Ser Pro Gln Phe Gln Tyr
        195                 200                 205

Gly Ser Lys Ala Tyr Val Lys His Pro Ala Asp Ile Pro Asp Tyr Leu
    210                 215                 220

Lys Leu Ser Phe Pro Glu Gly Phe Lys Trp Glu Arg Phe Met Asn Phe
225                 230                 235                 240

Glu Asp Gly Gly Val Val Thr Val Thr Gln Asp Ser Thr Leu Gln Asp
                245                 250                 255

Gly Glu Phe Ile Tyr Lys Val Lys Leu Arg Gly Thr Asn Phe Pro Ser
            260                 265                 270

Asp Gly Pro Val Met Gln Lys Lys Thr Met Gly Trp Glu Ala Ser Thr
        275                 280                 285

Glu Arg Met Tyr Pro Glu Asp Gly Ala Leu Lys Gly Glu Ile Lys Met
    290                 295                 300

Arg Leu Lys Leu Lys Asp Gly Gly His Tyr Asp Ala Glu Val Lys Thr
305                 310                 315                 320

Thr Tyr Lys Ala Lys Lys Gln Val Gln Leu Pro Gly Ala Tyr Met Thr
                325                 330                 335

Asp Ile Lys Leu Asp Ile Ile Ser His Asn Gly Asp Tyr Thr Ile Val
            340                 345                 350

Glu Gln Tyr Glu Arg Ala Glu Gly Arg His Ser Thr Gly Ala Gly Ser
        355                 360                 365

Ile Ile Arg Ser Ile Ile Ile His His His His His Ile Ala Ala
    370                 375                 380

Ala Pro Gly Leu Asp Leu Asn Ser Ile Leu Asp Arg Met Gln Ala Asp
385                 390                 395                 400

```
Phe Lys Cys Cys Gly Ala Ala Asn Tyr Thr Asp Trp Glu Lys Ile Pro
                405                 410                 415
Ser Met Ser Lys Asn Arg Val Pro Asp Ser Cys Cys Ile Asn Val Thr
            420                 425                 430
Val Gly Cys Gly Ile Asn Phe Asn Glu Lys Ala Ile His Lys Glu Gly
        435                 440                 445
Cys Val Glu Lys Ile Gly Gly Trp Leu Arg Lys Asn Val Leu Val Val
    450                 455                 460
Ala Ala Ala Leu Gly Ile Ala Phe Val Glu Val Leu Gly Ile Val
465                 470                 475                 480
Phe Ala Cys Cys Leu Val Lys Ser Ile Arg Ser Gly Tyr Glu Val Met
                485                 490                 495
Met Glu Ser Asp Glu Ser Gly Leu Pro Ala Met Glu Ile Glu Cys Arg
            500                 505                 510
Ile Thr Gly Thr Leu Asn Gly Val Glu Phe Glu Leu Val Gly Gly Gly
        515                 520                 525
Glu Gly Thr Pro Lys Gln Gly Arg Met Thr Asn Lys Met Lys Ser Thr
    530                 535                 540
Lys Gly Ala Leu Thr Phe Ser Pro Tyr Leu Leu Ser His Val Met Gly
545                 550                 555                 560
Tyr Gly Phe Tyr His Phe Gly Thr Tyr Pro Ser Gly Tyr Glu Asn Pro
                565                 570                 575
Phe Leu His Ala Ile Asn Asn Gly Gly Tyr Thr Asn Thr Arg Ile Glu
            580                 585                 590
Lys Tyr Glu Asp Gly Gly Val Leu His Val Ser Phe Ser Tyr Arg Tyr
        595                 600                 605
Glu Ala Gly Arg Val Ile Gly Asp Phe Lys Val Val Gly Thr Gly Phe
    610                 615                 620
Pro Glu Asp Ser Val Ile Phe Thr Asp Lys Ile Ile Arg Ser Asn Ala
625                 630                 635                 640
Thr Val Glu His Leu His Pro Met Gly Asp Asn Val Leu Val Gly Ser
                645                 650                 655
Phe Ala Arg Thr Phe Ser Leu Arg Asp Gly Gly Tyr Tyr Ser Phe Val
            660                 665                 670
Val Asp Ser His Met His Phe Lys Ser Ala Ile His Pro Ser Ile Leu
        675                 680                 685
Gln Asn Gly Gly Pro Met Phe Ala Phe Arg Arg Val Glu Glu Leu His
    690                 695                 700
Ser Asn Thr Glu Leu Gly Ile Val Glu Tyr Gln His Ala Phe Lys Thr
705                 710                 715                 720
Pro Ile Ala Phe Ala Arg Ser Arg Ala Gln Ser Ser Asn Ser Ala Val
                725                 730                 735
Asp Gly Thr Ala Gly Pro Gly Ser Thr Gly Ser Arg His His His His
            740                 745                 750
His His

<210> SEQ ID NO 8
<211> LENGTH: 473
<212> TYPE: PRT
<213> ORGANISM: Homo sapiens

<400> SEQUENCE: 8

Met Glu Ser Asp Glu Ser Gly Leu Pro Ala Met Glu Ile Glu Cys Arg
1               5                   10                  15
```

-continued

```
Ile Thr Gly Thr Leu Asn Gly Val Glu Phe Glu Leu Val Gly Gly
             20                  25                  30
Glu Gly Thr Pro Lys Gln Gly Arg Met Thr Asn Lys Met Lys Ser Thr
         35                  40                  45
Lys Gly Ala Leu Thr Phe Ser Pro Tyr Leu Leu Ser His Val Met Gly
 50                  55                  60
Tyr Gly Phe Tyr His Phe Gly Thr Tyr Pro Ser Gly Tyr Glu Asn Pro
 65                  70                  75                  80
Phe Leu His Ala Ile Asn Asn Gly Gly Tyr Thr Asn Thr Arg Ile Glu
                 85                  90                  95
Lys Tyr Glu Asp Gly Gly Val Leu His Val Ser Phe Ser Tyr Arg Tyr
             100                 105                 110
Glu Ala Gly Arg Val Ile Gly Asp Phe Lys Val Val Gly Thr Gly Phe
         115                 120                 125
Pro Glu Asp Ser Val Ile Phe Thr Asp Lys Ile Ile Arg Ser Asn Ala
     130                 135                 140
Thr Val Glu His Leu His Pro Met Gly Asp Asn Val Leu Val Gly Ser
145                 150                 155                 160
Phe Ala Arg Thr Phe Ser Leu Arg Asp Gly Gly Tyr Tyr Ser Phe Val
                 165                 170                 175
Val Asp Ser His Met His Phe Lys Ser Ala Ile His Pro Ser Ile Leu
             180                 185                 190
Gln Asn Gly Gly Pro Met Phe Ala Phe Arg Arg Val Glu Glu Leu His
         195                 200                 205
Ser Asn Thr Glu Leu Gly Ile Val Glu Tyr Gln His Ala Phe Lys Thr
     210                 215                 220
Pro Ile Ala Phe Ala Arg Ser Arg Ala Gln Ser Ser Asn Ser Ala Val
225                 230                 235                 240
Asp Gly Thr Ala Gly Pro Gly Ser Thr Gly Ser Arg Ser Arg Ala Ser
                 245                 250                 255
Glu Phe Met Ala Ser Arg Gly Ala Thr Arg Pro Asn Gly Pro Asn Thr
             260                 265                 270
Gly Asn Lys Ile Cys Gln Phe Lys Leu Val Leu Leu Gly Glu Ser Ala
         275                 280                 285
Val Gly Lys Ser Ser Leu Val Leu Arg Phe Val Lys Gly Gln Phe His
     290                 295                 300
Glu Phe Gln Glu Ser Thr Ile Gly Ala Ala Phe Leu Thr Gln Thr Val
305                 310                 315                 320
Cys Leu Asp Asp Thr Thr Val Lys Phe Glu Ile Trp Asp Thr Ala Gly
                 325                 330                 335
Gln Glu Arg Tyr His Ser Leu Ala Pro Met Tyr Tyr Arg Gly Ala Gln
             340                 345                 350
Ala Ala Ile Val Val Tyr Asp Ile Thr Asn Glu Glu Ser Phe Ala Arg
         355                 360                 365
Ala Lys Asn Trp Val Lys Glu Leu Gln Arg Gln Ala Ser Pro Asn Ile
     370                 375                 380
Val Ile Ala Leu Ser Gly Asn Lys Ala Asp Leu Ala Asn Lys Arg Ala
385                 390                 395                 400
Val Asp Phe Gln Glu Ala Gln Ser Tyr Ala Asp Asp Asn Ser Leu Leu
                 405                 410                 415
Phe Met Glu Thr Ser Ala Lys Thr Ser Met Asn Val Asn Glu Ile Phe
             420                 425                 430
Met Ala Ile Ala Lys Lys Leu Pro Lys Asn Glu Pro Gln Asn Pro Gly
```

-continued

```
            435                 440                 445
Ala Asn Ser Ala Arg Gly Arg Gly Val Asp Leu Thr Glu Pro Thr Gln
    450                 455                 460

Pro Thr Arg Asn Gln Cys Cys Ser Asn
465                 470
```